US011547364B2

(12) United States Patent
Kogure et al.

(10) Patent No.: US 11,547,364 B2
(45) Date of Patent: *Jan. 10, 2023

(54) ABNORMALITY NOTIFICATION SYSTEM, ABNORMALITY NOTIFICATION METHOD, AND PROGRAM

(71) Applicant: PARAMOUNT BED CO., LTD., Tokyo (JP)

(72) Inventors: Takamasa Kogure, Tokyo (JP); Tomoko Inoue, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 150 days.

This patent is subject to a terminal disclaimer.

(21) Appl. No.: 17/152,194

(22) Filed: Jan. 19, 2021

(65) Prior Publication Data

US 2021/0137462 A1    May 13, 2021

Related U.S. Application Data

(63) Continuation of application No. 15/757,495, filed as application No. PCT/JP2016/075766 on Sep. 2, 2016, now Pat. No. 10,925,545.

(30) Foreign Application Priority Data

Sep. 4, 2015    (JP) .................................. 2015-175003

(51) Int. Cl.
    *A61B 5/00*    (2006.01)
    *G08B 21/04*   (2006.01)
    (Continued)

(52) U.S. Cl.
    CPC .......... *A61B 5/7221* (2013.01); *A61B 5/0205* (2013.01); *A61B 5/4809* (2013.01);
    (Continued)

(58) Field of Classification Search
    CPC ... A61B 5/7221; A61B 5/0205; A61B 5/4809; A61B 5/6892; A61B 5/742; A61B 5/024;
    (Continued)

(56) References Cited

U.S. PATENT DOCUMENTS

| 10,238,351 B2 * | 3/2019 | Halperin ................ G16H 40/63 |
| 2008/0004499 A1 * | 1/2008 | Davis ..................... G16H 40/20 |
| | | 600/300 |

(Continued)

FOREIGN PATENT DOCUMENTS

| EP | 2 701 131 | 2/2014 |
| JP | 3557775   | 5/2004 |

(Continued)

OTHER PUBLICATIONS

International Search Report dated Dec. 6, 2016 in International (PCT) Application No. PCT/JP2016/075766.

(Continued)

*Primary Examiner* — Aditya S Bhat
(74) *Attorney, Agent, or Firm* — Wenderoth, Lind & Ponack, L.L.P.

(57) ABSTRACT

A biological signal of a subject is acquired so as to calculate biological information from the acquired biological signal. When the biological information has been determined to be anomaly, whether the biological information is one that was calculated under a high-accuracy condition is determined. When the biological information is determined to be one that was calculated under the high-accuracy condition, a notice is given based on a first criterion. In the other cases, a notice is given based on a second criterion. Thereby, it is possible to provide an abnormality notification system that can give a necessary notification appropriately while suppressing unnecessary notification, by changing the criteria for notification in accordance with the accuracy of the determined (Continued)

biological information when the biological information of the subject was determined to be anomaly.

16 Claims, 4 Drawing Sheets

(51) Int. Cl.
| | |
|---|---|
| *G08B 25/10* | (2006.01) |
| *G08B 25/08* | (2006.01) |
| *A61B 5/0205* | (2006.01) |
| *G08B 21/02* | (2006.01) |
| *A61B 5/024* | (2006.01) |
| *A61B 5/08* | (2006.01) |
| *A61B 5/11* | (2006.01) |
| *A61B 5/113* | (2006.01) |

(52) U.S. Cl.
CPC ............ *A61B 5/6892* (2013.01); *A61B 5/742* (2013.01); *G08B 21/0461* (2013.01); *G08B 25/08* (2013.01); *G08B 25/10* (2013.01); *A61B 5/024* (2013.01); *A61B 5/0816* (2013.01); *A61B 5/1102* (2013.01); *A61B 5/113* (2013.01); *A61B 5/7405* (2013.01); *G08B 21/02* (2013.01)

(58) Field of Classification Search
CPC ..... A61B 5/0816; A61B 5/1102; A61B 5/113; A61B 5/7405; G08B 21/0461; G08B 25/08; G08B 25/10; G08B 21/02

USPC ........................................................ 702/127
See application file for complete search history.

(56) References Cited

U.S. PATENT DOCUMENTS

| | | |
|---|---|---|
| 2011/0046498 A1 | 2/2011 | Klap |
| 2011/0112442 A1 | 5/2011 | Meger et al. |
| 2012/0253142 A1* | 10/2012 | Meger .................... A61B 5/113 |
| | | 600/301 |
| 2013/0267791 A1 | 10/2013 | Halperin |
| 2015/0164438 A1* | 6/2015 | Halperin ................ G16H 20/10 |
| | | 340/573.1 |

FOREIGN PATENT DOCUMENTS

| | | |
|---|---|---|
| JP | 2010-75761 | 4/2010 |
| JP | 2012-502671 | 2/2012 |
| JP | 2015-13046 | 1/2015 |
| WO | 2009/138976 | 11/2009 |
| WO | 2013/077288 | 5/2013 |
| WO | 2014/125402 | 8/2014 |

OTHER PUBLICATIONS

International Preliminary Report on Patentability and Written Opinion dated Mar. 6, 2018 in (PCT) International Patent Application No. PCT/JP2016/075766.

\* cited by examiner

|  | Upper Limit Threshold | Lower Limit Threshold |
|---|---|---|
| Heart Rate | 120 | 40 |
| Respiratory Rate | 30 | 5 |

| Criterion A | Equal to or greater than the upper limit threshold or equal to or lower than the lower limit threshold 3 times in succession |
|---|---|
| Criterion B | Equal to or greater than the upper limit threshold or equal to or lower than the lower limit threshold 10 times in succession |

ABNORMALITY NOTIFICATION SYSTEM, ABNORMALITY NOTIFICATION METHOD, AND PROGRAM

CROSS-REFERENCE TO RELATED APPLICATIONS

This application is a continuation of U.S. patent application Ser. No. 15/757,495, filed Mar. 5, 2018, which is a U.S. national stage application of the PCT International Application No. PCT/JP2016/075766 filed on Sep. 2, 2016, which claims the benefit of foreign priority of Japanese Patent Application No. 2015-175003, filed on Sep. 4, 2015.

TECHNICAL FIELD OF THE INVENTION

The present invention relates to an abnormality notification system and the like.

BACKGROUND ART

Apparatuses and systems for notifying patient abnormality have been conventionally known. For example, there is a known invention disclosed in Patent Document 1, in which the living behavior and biologic activities of a subject are detected by non-invasive type vital sensors and the detections are classified into a plurality of items, for each of which the permissible duration is successively accumulated, and when the cumulative time exceeds a threshold, a notification is given.

PRIOR ART DOCUMENTS

Patent Documents

Patent Document 1:
  Japanese Patent No. 3557775

SUMMARY OF THE INVENTION

Problem to be Solved

Conventionally, it is a common practice to make a notification based on whether or not a biological information value exceeds its threshold. For example, also in Patent Document 1 mentioned above, irrespective of the condition of the subject and the sensor characteristics, if the cumulative time of daily activity or life activity exceeds a predetermined threshold, it is judged to be abnormal and notification is made. However, accuracy varies depending on the condition of the target person and sensor characteristics. Therefore, since a notification is simply made irrespective of variation of these accuracies, there would occur a problem that a notification is made without reliability in some cases depending on the condition of the subject and the sensor characteristics.

Particularly, in the case of a system in a hospital or a nursing care facility used for notifying anomaly based on biological information, unnecessary abnormality notification based on an error or the like would impose a burden on medical personnel and staffs, which has been a problem.

In view of the above-described problems, it is therefore an object of the present invention is to provide an abnormality notification system or the like that can appropriately perform necessary notifications while suppressing unnecessary notifications by changing the condition for notifying according to the accuracy of the determined biological information when a type of biological information of a subject is determined to be anomaly.

An abnormality notification system of the present invention includes:
  a biological signal acquiring means for acquiring a biological signal of a subject;
  a biological information calculating means for calculating biological information from the acquired biological signal;
  an abnormality determining means for determining whether or not the biological information is anomaly;
  a condition determining means for determining whether the biological information is one that was calculated under a high-accuracy condition when the biological information has been determined to be anomaly by the abnormality determining means; and a notifying means that gives a notice based on a first criterion when the biological information is determined to be one that was calculated under the high-accuracy condition by the condition determining means and gives a notice based on a second criterion in the other case.

An abnormality notification method of the present invention includes:
  a biological signal acquiring step of acquiring a biological signal of a subject;
  a biological information calculating step of calculating biological information from the acquired biological signal;
  an abnormality determining step of determining whether or not the biological information is anomaly;
  a condition determining step of determining whether the biological information is one that was calculated under a high-accuracy condition when the biological information has been determined to be anomaly at the abnormality determining step; and a notifying step of giving a notice based on a first criterion when the biological information is determined to be one that was calculated under the high-accuracy condition at the condition determining step and giving a notice based on a second criterion in the other case.

Advantages of the Invention

According to the present invention, when it is determined that the biological information calculated based on the biological signal of the subject is abnormal, it is determined whether or not the biological information determined to be abnormal was calculated under the high-accuracy condition. Thereby, it is possible to give the notice of the anomaly based on criteria that are differentiated between the high-accuracy condition and other conditions.

For example, by switching the criteria between the first criterion of a loose standard applied to the high-accuracy condition and the second criterion of a strict standard applied to the low-accuracy condition, the notice of anomalies that originally need not be given is suppressed, and only necessary notification is performed.

MODE FOR CARRYING OUT THE INVENTION

Now, the best mode for carrying out the invention will be described with reference to the drawings. Specifically, an embodiment will be described in a case where an abnormality notification system of the present invention is applied, but the scope to which the present invention is applied is not limited to the embodiment.

1. First Embodiment

[1.1 Overall System]

Figure 1:
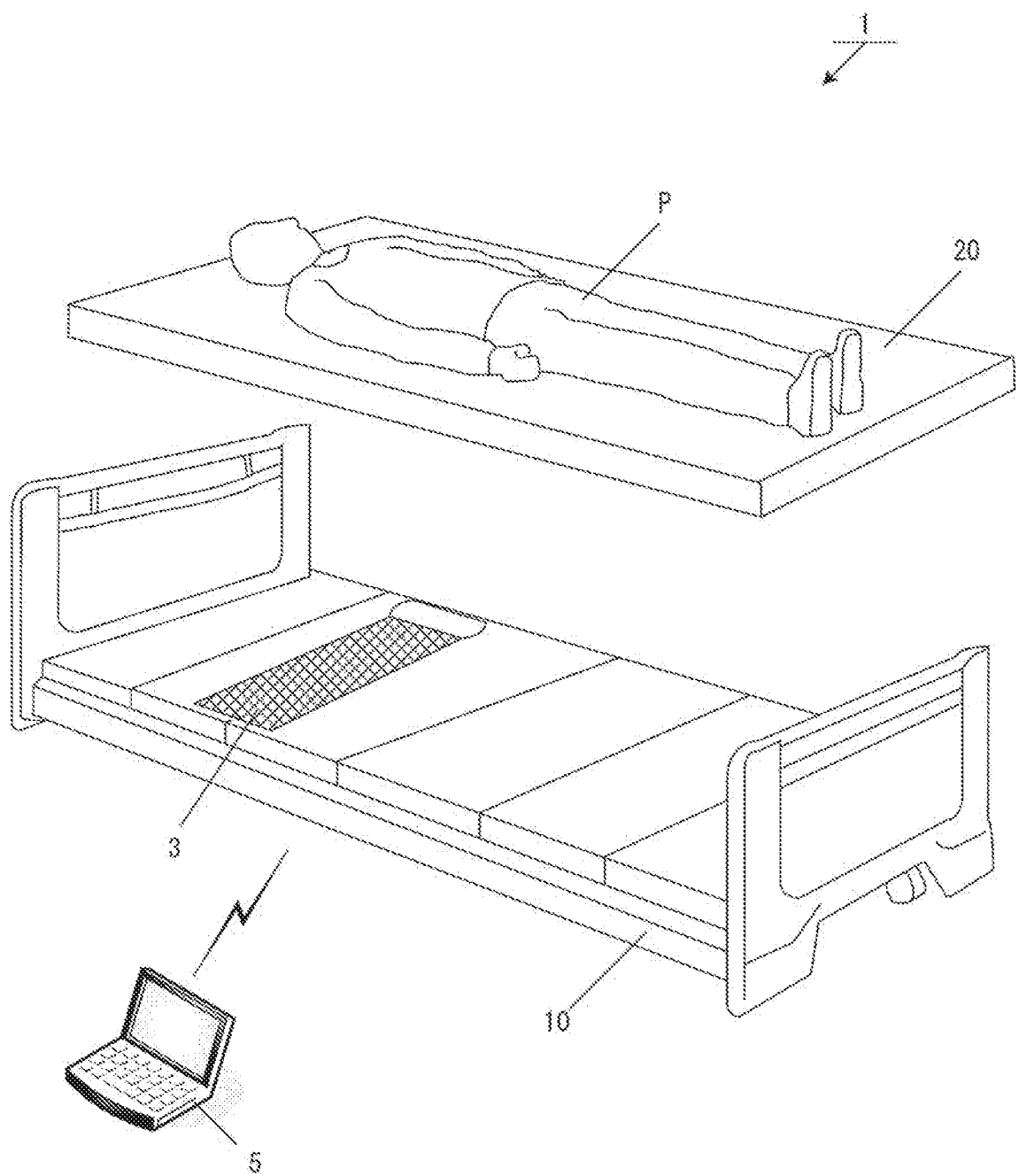
FIG. 1 A diagram for explaining the overall configuration of a first embodiment.

FIG. 1 is a diagram for explaining the overall outline of an abnormality notification system 1 to which the present invention is applied. As shown in FIG. 1, the abnormality notification system 1 includes a detection device 3 placed between a floor portion of a bed 10 and a mattress 20, a processing device 5 for processing output values from the detection device 3. The detection device 3 and the processing device 5 constitute a biological information output device.

When a subject (hereinafter referred to as, for example, "patient P") resides on the mattress 20, the detection device 3 detects the body motion (vibration) as the biological signal of the patient P. Then, based on the detected vibration, the biological information of the patient P is calculated. In the present embodiment, it is possible to output and display the calculated biological information (for example, respiratory rate, heart rate) as biological information of the patient P. For example, the detection device 3 may be integrally formed by providing a storage unit, a display unit and the like. Further, since the processing device 5 may employ a general-purpose device, the processing device is not limited to information processing devices such as computers and the like, but can be constituted of a device such as a tablet device and a smartphone, for example.

Also, the subject may be a person who is under medical treatment or needs care. Healthy persons who do not need nursing care, elder people, children, disabled people and even animals may be handled.

Here, the detection device 3 is shaped sheet-like so as to reduce its thickness. Thereby, even if the detection device is set between the bed 10 and the mattress 20, it can be used without causing the patient P to feel uncomfortable.

It should be noted that the detection device 3 only needs to acquire biological signals (such as body motion, respiratory motion, ballistocardiographic motion, etc.) of the patient P. Though in the present embodiment, the body motion is used to calculate the heart rate and the respiratory rate, it is possible, for example, to detect the body motion of the patient P by using an infrared sensor, to acquire biological signals of the patient P based on the acquired image, etc., or by using an actuator with a strain gauge.

[1.2 Functional Configuration]

Subsequently, the functional configuration of the abnormality notification system 1 will be described with reference to FIG. 2. The abnormality notification system 1 in the present embodiment includes the detection device 3 and the processing device 5, and each functional unit (process) other than a biological signal acquiring unit 200, may be realized by either of them.

In the abnormality notification system 1, the destination to which an anomaly is notified may be a staff member or a family member. In addition, as a method of notification, a notification (notice) may be made simply by sound or a screen display, or notice may be given to a portable terminal device by e-mail or the like. Further, notification (notice) may be given to other terminal devices and the like.

The abnormality notification system 1 includes a control unit 100, the biological signal acquiring unit 200, a biological information calculating unit 300, an input unit 400, an output unit 450, a storage unit 500 and a patient state acquiring unit 600. In the case of FIG. 1, the control unit 100, the biological signal acquiring unit 200 and the storage unit 500 are provided in the detection device 3 while the control unit 100, the biological information calculating unit 300, the input unit 400, the output unit 450 and the storage unit 500 are provided in the processing device 5. On the other hand, the patient state acquiring unit 600 may use the biological signal acquiring unit 200 or may be provided separately in the bed 10.

The control unit 100 is a functional unit for controlling the operation of the abnormality notification system 1, and may be configured of a control device such as a CPU and the like, or may be configured of a control device such as a computer or the like. The control unit 100 reads out and runs various programs stored in the storage unit 500 to realize various processes. In the present embodiment, the control unit 100 operates as a whole, but it may be provided separately in the detection device 3 and the processing device 5.

The biological signal acquiring unit 200 is a functional unit for acquiring biological signals of the patient P. In the present embodiment, as one example a sensor for detecting body motion of the patient P is used to acquire the body motion which is a kind of a biological signal. Then, the acquired body motion is output as body motion data. Based on this body motion data, various biological information of the patient P can be calculated. Further, based on the body motion data, it is also possible to grasp the condition of the patient P on the bed (for example, whether or not the patient P is lying on the bed, whether the patient P is staying on the bed, leaving the bed or sitting on the edge of the bed, etc.) and also grasp the sleep state (sleeping, awakening) of the patient.

In the present embodiment, the biological signal acquiring unit 200 acquires the vibration (body motion) of the patient by means of a pressure sensor, for example, and acquires breathing and heartbeat from the vibration. However, a load sensor may be used to detect change of the position of the center of gravity (body motion) of the patient, thereby acquire the biological information signal, or a microphone may be provided to acquire biological information based on the sound picked up by the microphone. Any sensor may be used as long as biological signals of the patient can be obtained.

That is, the biological signal acquiring unit 200 may be connected to a device such as the detection device 3, or it is also possible to provide a configuration that the biological signal acquiring unit 200 receives biological signals from external devices.

The biological information calculating unit 300 is a functional unit for calculating biological information (respiratory rate, heart rate, etc.) of the patient P. In the present embodiment, the respiration component/heart rate component may be extracted from the body motion acquired from the biological signal acquiring unit 200 so as to determine the respiratory rate and heart rate based on the respiration interval and heartbeat interval. Alternatively, the periodicity of the body motion may be analyzed (by Fourier transform, etc.), to calculate the respiratory rate and heart rate from the peak frequencies.

The input unit 400 is a functional unit for allowing the measurer to input various conditions and perform operation input for starting measurement. This function is, for example, implemented by hardware keys, software keys or some other input means.

The output unit 450 is a functional unit for outputting the sleep state and biological information such as heart rate and respiratory rate and notifying anomalies of biological information. The output unit 450 may be a display device such as a display or a notification device (sound output device) for giving an alarm or the like. Further, it may be an external storage device that stores data, a transmitter that transmits data via a communication path, and the like. Further, it may be a communication device for reporting to other devices.

The storage unit 500 is a functional unit that stores various data and programs for the abnormality notification system 1 to operate. The control unit 100 reads out and runs the program stored in the storage unit 500 to realize various functions. Here, the storage unit 500 is composed of, for example, a semiconductor memory, a magnetic disk device and/or the like. In this case, the storage unit 500 stores biological information data 510, a reference value table 512, a notification criteria setting table 514 and a condition decision table 516.

Stored in the biological information data 510 are the respiratory rate and heart rate calculated from the acquired biological signal (body motion). Though, in the present embodiment, both the respiratory rate and the heart rate are stored, only one of them may be stored. Further, other information (for example, variations in respiration amplitude) may be stored as long as it is biological information that can be calculated by the biological information calculating unit 300.

The reference value table 512 stores reference values (that is, reference values and thresholds based on which anomaly is determined) of the biological information to be notified. For example, as shown in FIG. 3, an upper limit threshold and a lower limit threshold of each biological information are stored. For example, for the heart rate the upper limit threshold is stored as "120" and the lower limit threshold as "40". When the detection becomes equal to or higher than the upper limit threshold or falls below the lower limit threshold, the biological information is determined to be abnormal.

Here, in the present embodiment the reference value table 512 is stored for the upper limit thresholds and the lower limit thresholds but the reference value table 512 only needs to store the conditions to be notified. For example, the upper limit thresholds and the lower limit thresholds may be stored in association with the sleeping state and the awakening state. Or the upper limit threshold and the lower limit threshold are stored in association with the operation state (actuated state/still state) of the air mat.

The notification criteria setting table 514 is a table for storing criteria based on which it is determined whether or not notice of an anomaly value is given when the biological information is determined to be abnormal. Here, the anomaly value is a value (heart rate/respiratory rate) when the biological information is determined to be abnormal.

Figures 2, 3, 4:
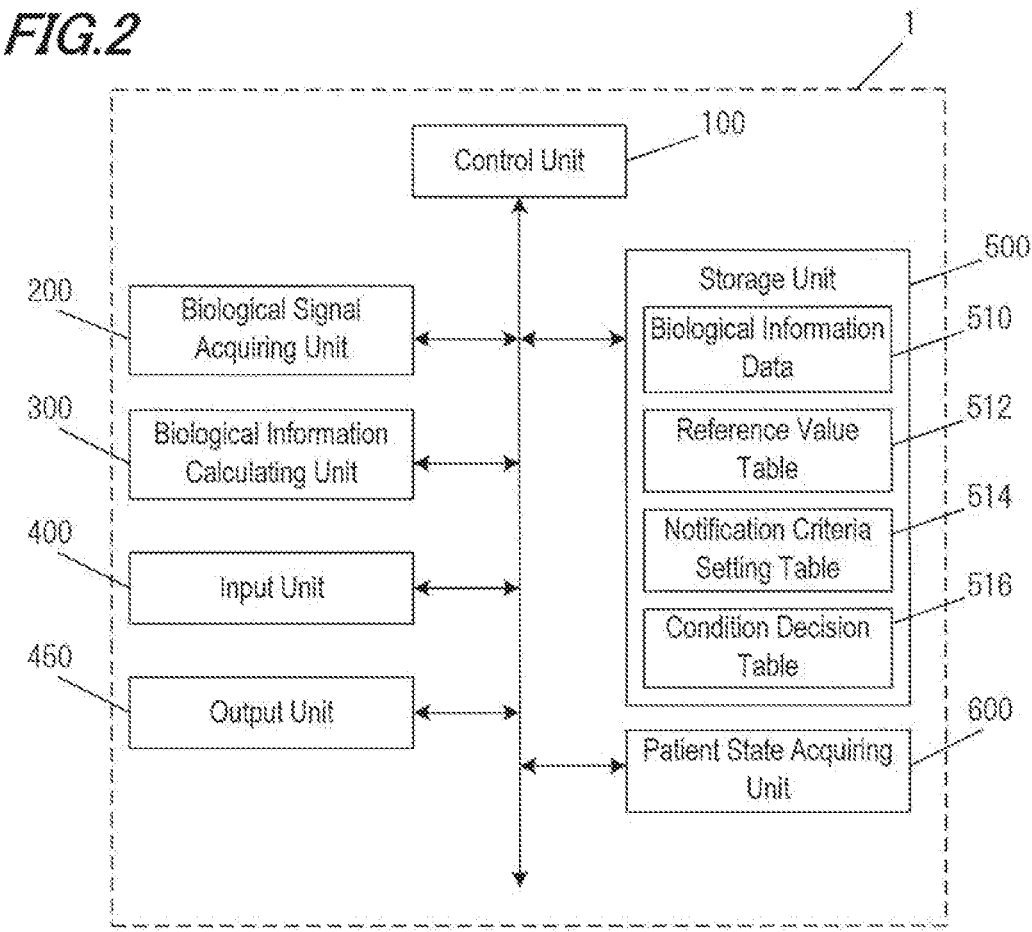
FIG. 2 A diagram for explaining a functional configuration in the first embodiment.
FIG. 3 A diagram showing one example of a data configuration in a reference value table in the first embodiment.
FIG. 4 A diagram showing one example of a data configuration in a notification criteria setting table in the first embodiment.

Further, in the present embodiment, as shown in FIG. 4 a criterion A indicating the criterion for high-accuracy anomaly values output as anomaly values under high-accuracy condition and a criterion B indicating the criterion for the other anomaly values (low-accuracy anomaly value) are stored. Note that the criteria may be set more finely or may be set for each biological information. Here, the high-accuracy anomaly value is an anomaly value that is output when the condition under which the biological information was determined to be abnormal meets high-accuracy condition, whereas an anomaly value output under other than the high-accuracy condition should be determined as a low-accuracy anomaly value.

In addition, the criteria may be set depending on the time periods. For example, different criteria may be set in accordance with the variation in accuracy depending on time periods found out from past notifying histories. Also, a plurality of criteria may be switched over depending on the state of the patient P such as the sleeping state or the awake state, the operation state (actuated state/still state) of the air mat, and the characteristics of the patient (for example, individual characteristics such as the medical condition, age, etc.).

The condition decision table 516 is a table storing the conditions that can be used to determine whether the biological information was determined based on the high-accuracy condition (the high-accuracy anomaly value) or the low-accuracy condition (the low-accuracy anomaly value) when the biological information was determined to be anomaly. For example, the stored high-accuracy condition may include states of the patient P sleeping and being recumbent, and an operating state (still state) of the air mat. Note that the low-accuracy condition may be stored, which may include, for example, a state of the patient P being awake, a state of the patient P being not recumbent and a state of the air mat being actuated.

The patient state acquiring unit 600 is a functional unit for acquiring the state of the patient. For example, a load sensor or the like arranged in the bed 10 is used to grasp the state of the patient (leaving bed, staying in bed, etc.). As described above, this function can be implemented by the biological signal acquiring unit 200.

[1.3 Processing Flow]

Subsequently, the flow of the processing of the abnormality notification system 1 in the present embodiment will be described. First, body motion is acquired. Specifically, body motion data is acquired as a kind of biological signal from the biological signal acquiring unit 200 (Step S102). As the body motion data, it is possible to acquire it by, for example, detecting vibration.

Subsequently, the biological information calculating unit 300 calculates biological information (Step S104). In the present embodiment, the body motion acquired as a biological signal is separated into a respiratory component and a heartbeat component so as to calculate heart rate and respiratory rate as biological information.

Here, various methods can be considered as methods for calculating heart rate and respiratory rate. For example, the body motion data is filtered so as to extract the respiratory component and determine the breath interval for each breath. Then, the respiratory rate is calculated based on the breath interval. Also, the body motion data is filtered to extract the heart beat component and determine the heart beat interval for each beat. Then, the heart rate is calculated based on the heart beat interval.

Alternatively, calculation may be performed by analyzing the periodicity of the body motion data to find the respiratory rate and the heart rate from the peak frequencies.

Further, in the present embodiment, values calculated on the basis of body motion data, for example every 5 seconds are used. Specifically, calculation is performed every 5 seconds based on the heart rate and/or the respiratory rate calculated during a predetermined period of time. In the present embodiment, both the heart rate and the respiratory rate are calculated, but calculation may be performed for either one of them alone.

Subsequently, the biological information calculated at Step S104 is output (Step S106). The output destination may be a display device such as a display monitor or a device such as a mobile terminal device located at a remote site. Further, the output may be given as a print or e-mail transmission, or may be simply stored. That is, biological information (for example, heart rate, respiratory rate) may be output in any form as long as it is output.

Next, it is determined whether or not the calculated biological information is anomaly, that is, whether the heart rate and/or the respiratory rate take abnormal values (Step S108). Specifically, compared with the reference value table 512, it is determined whether either of the heart rate and the respiratory rate is equal to or higher than the upper limit threshold or equal to or lower than the lower limit threshold. Here, determination may be made without including the threshold (e.g., the value may be less than the lower limit threshold).

Here, when the biological information is determined to be abnormal (Step S108: Yes), instead of starting a notifying process immediately, it is determined whether or not the value (anomaly value) determined to be anomaly is the high-accuracy anomaly value. That is, when the biological information was determined to be abnormal, it is determined whether the condition for which the biological information was calculated is the high-accuracy condition (for example, if the heart rate was used, whether the heart rate is equal to or lower than the lower limit threshold, and if the respiratory rate was used, whether the respiratory rate is equal to or higher than the upper limit threshold) (Step S110).

If the value is determined to be the high-accuracy anomaly value, a notifying process is effected if the criterion A is satisfied (Step S110; Yes→Step S112). If the condition at Step S110 is not satisfied, the biological information is one calculated under the low-accuracy condition. Therefore, if the criterion B is satisfied, the notifying process is executed (Step S110; No→Step S114).

Here, heart rate or respiratory rate is used for judgment of the high-accuracy condition/low-accuracy condition in the present embodiment. The criteria are stored in the notification criteria setting table 514. Although conditions may be set for each of them, in the present embodiment it is determined whether or not calculation is performed under the high-accuracy condition, and the biological information that does not meet the high-accuracy condition is determined to be one calculated under the low-accuracy condition.

Next, as the method of determining whether or not the condition is the high-accuracy condition, the case where heart rate is used as a reference and the case where respiratory rate is used as a reference will be described. Note that these decisions may be made individually or in combination.

(1) The Case where Heart Rate is Used as a Reference

For example, since the probability of error is small when the heart rate is equal to or lower than the lower limit threshold (e.g., "40" or lower), the biological information should be one that is calculated under high-accuracy condition. Therefore, when the biological information is abnormal (taking an anomaly value), the value is determined to be the high-accuracy anomaly value. Conversely, when the heart rate is equal to or higher than the upper limit threshold (e.g., "120" or greater), the value is determined to be the low-accuracy anomaly value because there is a risk that non-anomaly value is erroneously determined to be an anomaly value due to a reason such as counting of vibrations other than the heartbeat as heartbeats. Therefore, when the heart rate is equal to or lower than the lower limit threshold, the reliability of the calculated anomaly value is determined to be high so that the criterion A is applied. That is, when the biological information is judged to be abnormal three times in succession, it is decided that an anomaly has been detected and a notifying process is executed.

Conversely, when the reliability of the biological information determined to be abnormal is decided to be low, the criterion B is applied. That is, when the biological information is determined to be abnormal for ten consecutive times, it is decided that an anomaly has been detected and a notifying process is executed.

(2) The Case where the Respiratory Rate is Used as a Reference

For example, since the probability of error is small when the respiratory rate is equal to or higher than the upper limit threshold (e.g., "30" or greater), the biological information should be one that is calculated under the high-accuracy condition. Therefore, when the biological information is abnormal (taking an anomaly value), the value is determined to be the high-accuracy anomaly value. Conversely, when the respiratory rate is equal to or lower than the lower limit threshold (e.g., "5" or less), the provability of error that the value is erroneously determined to be an anomaly value becomes high due to a reason such as small input of vibration because of lack of recumbent state or others. Therefore, when the respiratory rate is equal to or higher than the upper limit threshold, the reliability of the biological information determined to be abnormal is high (high-accuracy anomaly value), so that the criterion A is applied. That is, when the biological information is judged to be abnormal three times in succession (exceeding the upper limit threshold), it is decided that an anomaly has been detected and a notifying process is executed.

Conversely, when the reliability of the biological information determined to be abnormal is low (low-accuracy anomaly value), the criterion B is applied. That is, when the biological information is judged to be abnormal for ten consecutive times, it is determined that an anomaly has been detected and a notifying process is executed.

[1.4 Application Example and Effect]

Figure 6:
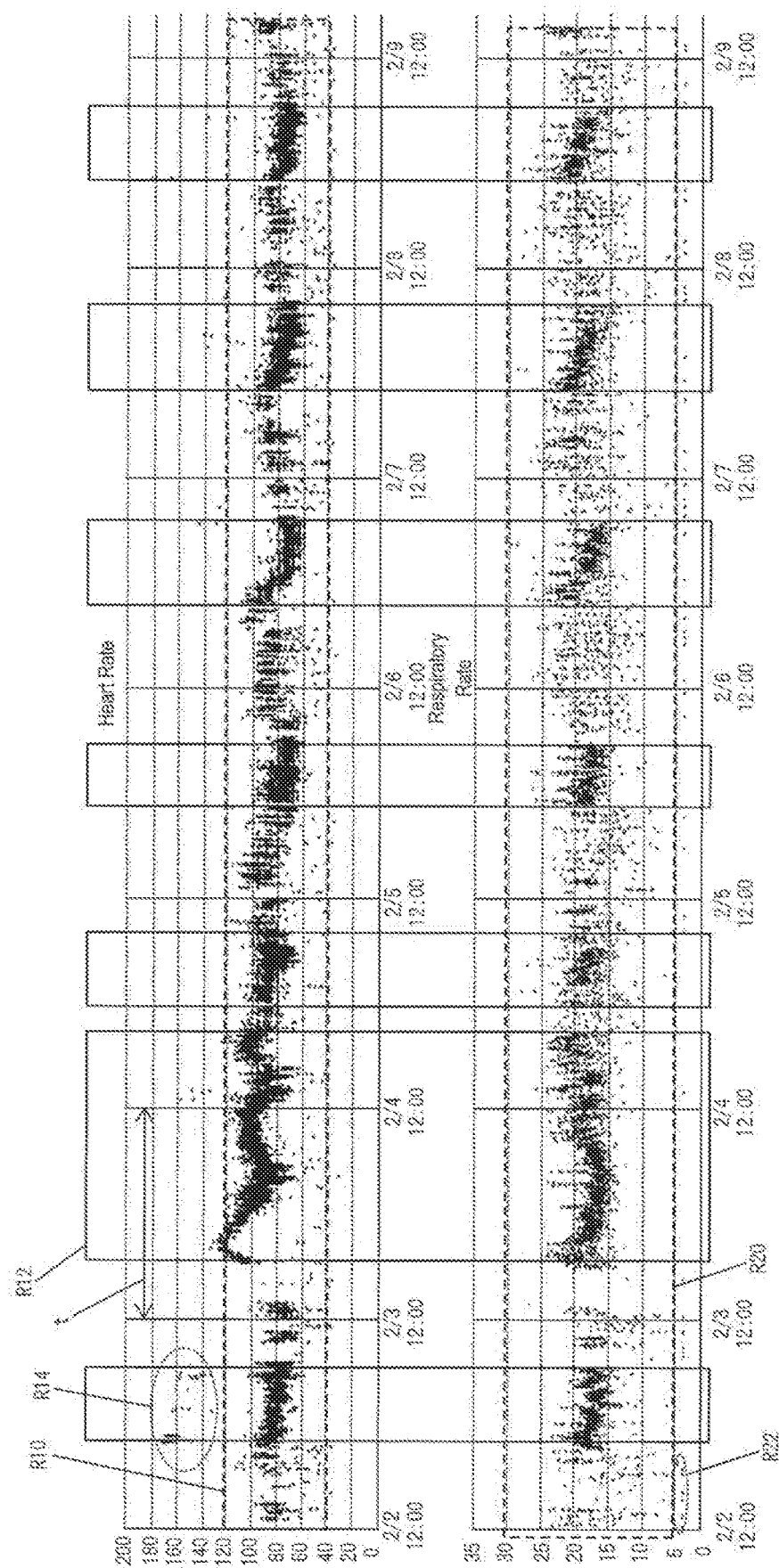
FIG. 6 A chart for explaining applied examples in the first embodiment.

A case where the abnormality notification system 1 according to the present embodiment is applied will be described with reference to FIG. 6. FIG. 6 shows a graph of heart rate on the upper side and a graph of respiratory rate on the lower side. Here, an interval t is the length of a day, and the areas indicated by the dotted lines show normal ranges. For example, the normal range of heart rate is the range R10 (40 to 120), and the normal range of respiratory rate is the range R20 (5 to 30).

Also, the areas framed by the black lines show the sleeping period. For example, a frame R12 is a sleeping period of the patient P. Points falling outside the normal range present anomaly values (in this case, all points are error portions). For example, a region R14 in heart rate and a region R22 in the respiratory rate are error portions.

As to this patient, no anomaly values occurred with the wearing type electrocardiograph, so that it is considered that there were no true anomaly values. However, as shown in FIG. 6, with the non-wearable device which is inferior in reliability to wearable type it turns out that anomaly values (that is, low-accuracy anomaly values) were calculated for heart rate equal to or higher than the upper limit threshold and for respiratory rate equal to or lower limit threshold. All of these anomaly values are those that do not need to be notified due to measurement errors. For low-accuracy anomaly values, it is possible to restrain unnecessary notification by tightening the criterion for granting execution of a notifying process.

In the case of this example, unnecessary notification can become 0 time by applying this embodiment. That is, with low-accuracy anomaly values including many errors, unnecessary notification is restrained by tightening the criterion for notification.

As described above, according to the present embodiment, it is possible to determine the accuracy of an anomaly value at the time of anomaly judgement and change the criteria for notification depending on the accuracy of the anomaly value. Since the criteria involve weighting, it is possible to perform highly accurate notifying and notification.

Thus, when abnormalities are notified, it is possible to reduce false alarms and notify anomalies with improved reliability. Since occurrence of false notice degrades nursing efficiency, it is necessary to suppress false notice. Furthermore, frequent notifications including many false notices become prone to be ignored by the medial personnel and staffs, which ends up increase of the risk of an actual anomaly being overlooked. Notification with a reduced ratio of false notice enables medical personnel, staff, etc. to perform appropriate action when an anomaly occurs in the subject.

2. Second Embodiment

Subsequently, a second embodiment will be described. In the first embodiment, high-accuracy anomaly values are determined using the biological information such as the heart rate and the respiratory rate. In this embodiment the high-accuracy anomaly values are determined based on whether the patient is in an awakening condition or sleeping condition.

FIG. 6 shows an outline of a sleeping section (frame R12 and the like) (though awakening portions actually exist in the illustrated sleeping section), from which it is understood that the sleeping section presents high-accuracy measurements with few anomaly values and small measurement variations. It is considered that stable measurement can be done during sleep because the body is stationary for long time. The anomaly values output during sleep is taken as high-accuracy anomaly values.

Figure 5:
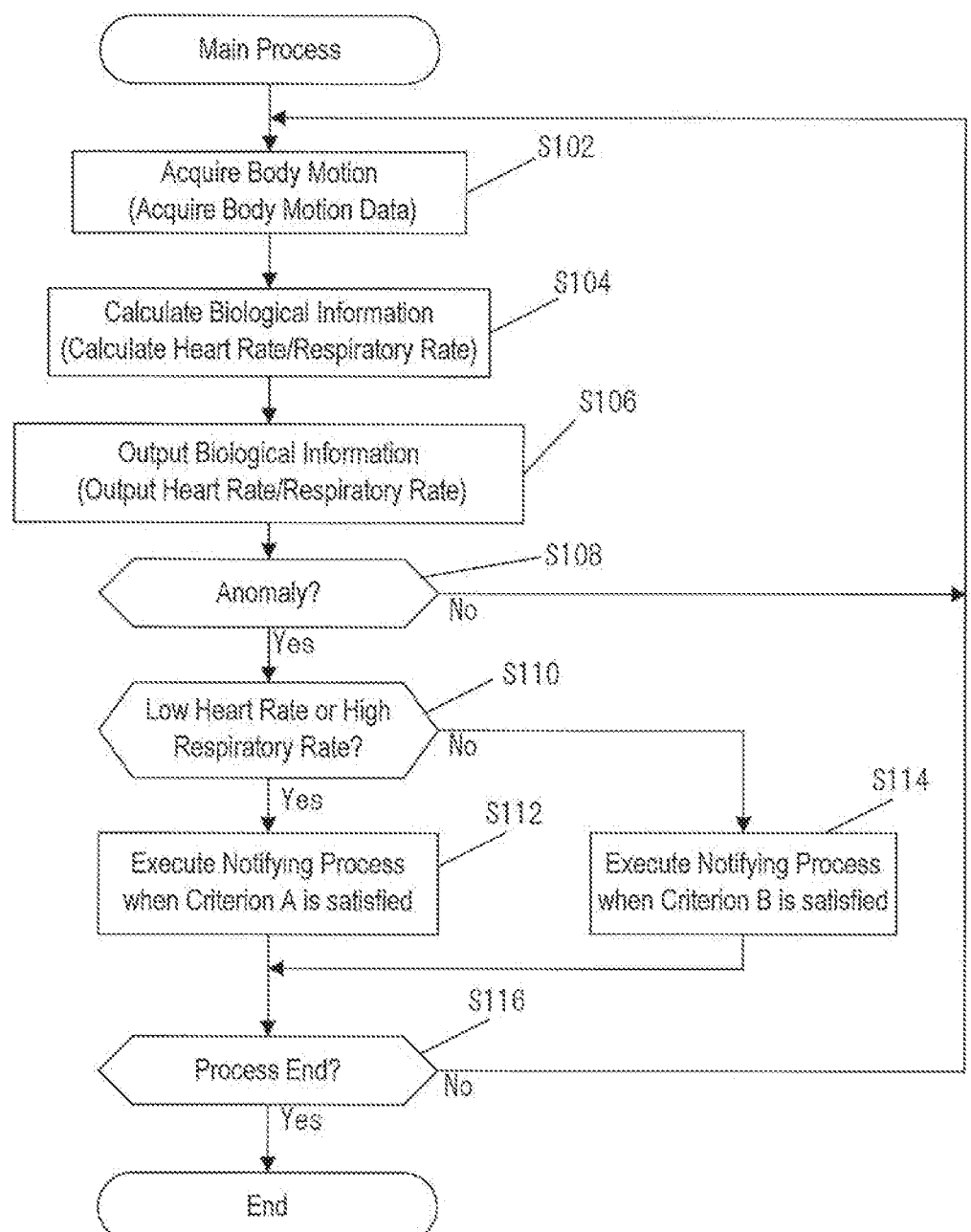
FIG. 5 An example of an operation flow in the first embodiment.

Specifically, at Step S110 in FIG. 5, it is determined whether or not the patient is "sleeping". Whether or not the patient P is sleeping may be determined by any known method and can be determined based on body motion data or based on a separate sleep state detecting device.

If the patient is sleeping, the condition is determined to be the high-accuracy condition, and a notifying process is executed according to the criterion A (Step S110; Yes→Step S112). On the other hand, in the case of awakening, a notifying process is executed in accordance with criterion B (Step S110; No→Step S114).

As described above, according to this embodiment, it is possible to change the criteria for performing a notifying process according to the sleeping state of the patient P. Here, this embodiment may be effected in combination with the first embodiment. In this case, when, for example, notification needs to be suppressed, a notifying process is executed based on the criterion A when the high-accuracy condition in the first embodiment is determined and when the patient is sleeping. As another example, it is also possible to perform judgment based on the criterion A during sleep and use the method of judgement according to the first embodiment during awakening. That is, since each processing is independent, it is possible to combine them appropriately as necessary.

3. Third Embodiment

Next, a third embodiment will be described. In the third embodiment, when the system is connected to an external device such as an air mat (a state detection device) that generates vibration, the measurement is handled as a low-accuracy anomaly value during the air mat is operated by the state detection device.

That is, at Step S110 in FIG. 5, when the state detection device detects that air mat is being operated, the output anomaly value is regarded as a value based on the biological information calculated under the low-accuracy condition, a notifying process is executed based on the criterion B (Step S110; No→Step S114).

According to the present embodiment, in addition to the first embodiment and the second embodiment, it is possible to obtain an effect that more unnecessary notification can be suppressed. It goes without saying that this embodiment may be used in combination with any of the processing of the first embodiment and the second embodiment.

4. Variational Examples

Although the embodiments of the present invention have been described in detail with reference to the drawings, the specific configuration should not be limited to the above embodiments. Designs and others that do not depart from the gist of the present invention should also be included in the scope of claims.

Note that the detection device 3 in the above-described embodiments may be one that is simply placed on the mattress 20 to detect the body motion of the patient P. In this case, the system can be realized simply by using, for example a smartphone or the like though the detection accuracy may degrade.

Further, though description of the present embodiment has been made by using body motion as an example of a biological signal, for example, a temperature (to calculate the respiratory rate by measuring the temperature of nasal breathing), a blood flow (measuring pulses using the light absorption amount) and other biological signals may be used.

DESCRIPTION OF REFERENCE NUMERALS 1 abnormality notification system
3 detection device
5 processing device
10 bed
20 mattress
100 control unit
200 biological signal acquiring unit
300 biological information calculating unit
400 input unit
450 output unit
500 storage unit
510 biological information data
512 reference value table
514 notification criteria setting table
516 condition decision table
600 patient state acquiring unit

The invention claimed is:

1. A bio-information accuracy determining system comprising:
   a bed;
   a sensor on the bed configured to acquire body motion data of a user;
   control circuitry configured to:
   calculate bio-information of the user from the body motion data,
   determine whether the calculated bio-information is high-accuracy bio-information or low-accuracy bio-information by analyzing the calculated bio-information with respect to criteria, when the calculated bio-information is abnormal, whether the calculated bio-information is high-accuracy bio-information or low-accuracy bio-information being determined as follows: if the respiratory rate is equal to or higher than an upper limit threshold, or if the heart rate is equal to or lower than a lower limit threshold, the calculated bio-information is determined to be high-accuracy bio-information and if the respiratory rate is equal to or lower than a lower limit threshold or if the heart rate is equal to or higher than an upper limit threshold, the calculated bio-information is determined to be low-accuracy bio-information,
   output a first notification using both a first rule and the calculated bio-information if the calculated bio-information is determined to be high-accuracy bio-information, and
   output a second notification using both a second rule and the calculated bio-information if the calculated bio-information is determined to be low-accuracy bio-information, the first rule being different from the second rule.

2. The bio-information accuracy determining system according to claim 1, wherein:
   the second rule is requiring a larger number in succession of judgments of abnormality of the calculated bio-information than the first rule.

3. The bio-information accuracy determining system according to claim 2, wherein:
   the control circuitry calculates a heart rate and/or a respiratory rate of the user as the bio-information from the body motion data, and determines that the biological information is high accuracy bio-information when the heart rate is lower than a reference threshold or when the respiratory rate is higher than a reference threshold.

4. The bio-information accuracy determining system according to claim 3, wherein:
   the control circuitry determines that the biological information is high-accuracy bio-information when it is determined that the user is sleeping.

5. The bio-information accuracy determining system according to claim 1, wherein:
   the control circuitry determines that the biological information is high-accuracy bio-information when it is determined that the user is sleeping.

6. The bio-information accuracy determining system according to claim 1, further comprising an operation detector that detects an operation of an external vibration device, wherein:
   the control circuitry determines that the biological information is low-accuracy bio-information when the operation detector detects an operation of the external vibration device.

7. A bio-information accuracy determining method comprising:
   acquiring body motion data of a user on a bed;
   calculating, with control circuitry, bio-information of the user from the body motion data,
   determining, with the control circuitry, whether the calculated bio-information is high accuracy bio-information or low-accuracy bio-information by analyzing the calculated bio-information with respect to criteria, when the calculated bio-information is abnormal, whether the calculated bio-information is high-accuracy bio-information or low-accuracy bio-information being determined as follows: if the respiratory rate is equal to or higher than an upper limit threshold, or if the heart rate is equal to or lower than a lower limit threshold, the calculated bio-information is determined to be high-accuracy bio-information and if the respiratory rate is equal to or lower than a lower limit threshold or if the heart rate is equal to or higher than an upper limit threshold, the calculated bio-information is determined to be low-accuracy bio-information;
   outputting, with the control circuitry, a first notification using both a first rule and the calculated bio-information if the calculated bio-information is determined to be high-accuracy bio-information, and
   outputting, with the control circuitry, a second notification using both a second rule and the calculated bio-information if the calculated bio-information is determined to be low-accuracy bio-information, the first rule being different from the second rule.

8. The bio-information accuracy determining method according to claim 7,
   the second rule is requiring a larger number in succession of judgments of abnormality of the calculated bio-information than the first rule.

9. The bio-information accuracy determining method according to claim 7, comprising calculating a heart rate and/or a respiratory rate of the user as the bio-information from the body motion data, and determining that the biological information is high accuracy bio-information when the heart rate is lower than a reference threshold or when the respiratory rate is higher than a reference threshold.

10. The bio-information accuracy determining method according to claim 9, comprising determining that the biological information is high-accuracy bio-information when it is determined that the user is sleeping.

11. The bio-information accuracy determining method according to claim 7, comprising determining that the biological information is high-accuracy bio-information when it is determined that the user is sleeping.

12. A non-transitory computer readable medium having stored thereon a program for causing a computer to execute a bio-information accuracy determining method comprising:
    acquiring body motion data of a user on a bed;
    calculating, with control circuitry, bio-information of the user from the body motion data;
    determining, with the control circuitry, whether the calculated bio-information is high accuracy bio-information or low-accuracy bio-information by analyzing the calculated bio-information with respect to criteria, when the calculated bio-information is abnormal, whether the calculated bio-information is high-accuracy bio-information or low-accuracy bio-information being determined as follows: if the respiratory rate is equal to or higher than an upper limit threshold, or if the heart rate is equal to or lower than a lower limit threshold, the calculated bio-information is determined to be high-accuracy bio-information and if the respiratory rate is equal to or lower than a lower limit threshold or if the heart rate is equal to or higher than an upper limit threshold, the calculated bio-information is determined to be low-accuracy bio-information;

outputting, with the control circuitry, a first notification using both a first rule and the calculated bio-information if the calculated bio-information is determined to be high-accuracy bio-information, and outputting, with the control circuitry, a second notification using both a second rule and the calculated bio-information if the calculated bio-information is determined to be low-accuracy bio-information, the first rule being different from the second rule.

13. The bio-information accuracy determining method according to claim 12, comprising determining that the biological information is low-accuracy bio-information if an operation of an external vibration device is detected.

14. The non-transitory computer readable medium according to claim 12, wherein:
the second rule is requiring a larger number in succession of judgments of abnormality of the calculated bio-information than the first rule.

15. The non-transitory computer readable medium according to claim 12, wherein the method comprises calculating a heart rate and/or a respiratory rate of the user as the bio-information from the body motion data, and determining that the biological information is high-accuracy bio-information when the heart rate is lower than a reference threshold or when the respiratory rate is higher than a reference threshold.

16. The non-transitory computer readable medium according to claim 12, wherein the method comprises determining that the biological information is high-accuracy bio-information when it is determined that the user is sleeping.

* * * * *